United States Patent
Beynnon et al.

(10) Patent No.: US 7,387,644 B2
(45) Date of Patent: Jun. 17, 2008

(54) KNEE JOINT PROSTHESIS WITH A FEMORAL COMPONENT WHICH LINKS THE TIBIOFEMORAL AXIS OF ROTATION WITH THE PATELLOFEMORAL AXIS OF ROTATION

(75) Inventors: Bruce D. Beynnon, South Burlington, VT (US); Stephen J. Incavo, South Burlington, VT (US); Kathryn M. Coughlin, Hinesburg, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 196 days.

(21) Appl. No.: 10/938,747

(22) Filed: Sep. 10, 2004

(65) Prior Publication Data

US 2005/0102032 A1 May 12, 2005

Related U.S. Application Data

(60) Provisional application No. 60/518,351, filed on Nov. 7, 2003.

(51) Int. Cl.
*A61F 2/38* (2006.01)
(52) U.S. Cl. .................. 623/20.15; 623/20.14
(58) Field of Classification Search ............ 623/13.12, 623/20.14, 20.18, 20.19, 20.21, 20.23, 20.26, 623/20.35, 22.4, 23.11–23.15, 20.3, 23.39, 623/20.31, 20.25; 606/88, 89
See application file for complete search history.

(56) References Cited

U.S. PATENT DOCUMENTS 4,081,866 A 4/1978 Upshaw et al.

(Continued)

FOREIGN PATENT DOCUMENTS

EP 0582514 2/1994

(Continued)

OTHER PUBLICATIONS

Incavo et al., "The Tibial Axis and Patellar Position in Knee Kinematics", American Association of Hip and Knee Surgeons, Eleventh Annual Meeting, Nov. 9-11, 2001, Dallas, Texas., p. 32.

(Continued)

*Primary Examiner*—Corrine McDermott
*Assistant Examiner*—Christopher Daniel Prone
(74) *Attorney, Agent, or Firm*—Wolf Greenfield & Sacks, P.C.

(57) ABSTRACT

A femoral component is provided for use in a knee joint prosthesis. The femoral component may be configured to provide one or more desirable kinematic relationships with a tibial component and/or patella so as to mimic the flexion and extension motion of a natural knee joint. The femoral component may be configured so that the patella follows a substantially circular pathway during knee flexion and extension. The femoral component may be configured so that the patella follows a curved patellar path during flexion and extension, and the curved patellar path has an origin located anterior and proximal to the geometrical center axis of the knee. The femoral component may be configured so that the patella follows a curved patellar path that lies in a plane which is parallel to and offset from a plane that extends through the center of the femoral head of a femur and is perpendicular to the geometric center axis of the knee. The femoral component may be configured so that at least a portion of the patella substantially follows a patellar path in a plane perpendicular to the geometrical center axis of a knee throughout knee flexion.

14 Claims, 4 Drawing Sheets

U.S. PATENT DOCUMENTS

| | | | |
|---|---|---|---|
| 4,213,209 A | | 7/1980 | Insall et al. |
| 4,944,756 A | | 7/1990 | Kenna |
| 5,021,061 A | | 6/1991 | Wevers et al. |
| 5,035,700 A | | 7/1991 | Kenna |
| 5,133,758 A | | 7/1992 | Hollister |
| 5,234,433 A | | 8/1993 | Bert et al. |
| 5,271,747 A | * | 12/1993 | Wagner et al. ............ 623/20.27 |
| 5,326,361 A | | 7/1994 | Hollister |
| 5,480,444 A | | 1/1996 | Incavo et al. |
| 5,601,566 A | | 2/1997 | Dance et al. |
| 5,681,354 A | | 10/1997 | Eckhoff |
| 5,683,471 A | | 11/1997 | Incavo et al. |
| 5,702,466 A | | 12/1997 | Pappas et al. |
| 5,728,162 A | | 3/1998 | Eckhoff |
| 5,766,257 A | | 6/1998 | Goodman et al. |
| 5,824,100 A | | 10/1998 | Kester et al. |
| 5,824,105 A | * | 10/1998 | Ries et al. ............... 623/20.31 |
| 5,871,546 A | | 2/1999 | Colleran et al. |
| 5,906,643 A | | 5/1999 | Walker |
| 5,935,173 A | * | 8/1999 | Roger et al. ............. 623/20.31 |
| 6,013,103 A | * | 1/2000 | Kaufman et al. ........ 623/20.15 |
| 6,039,764 A | | 3/2000 | Pottenger et al. |
| 6,342,075 B1 | | 1/2002 | MacArthur |
| 6,972,039 B2 | * | 12/2005 | Metzger et al. .......... 623/20.29 |
| 2001/0037155 A1 | | 11/2001 | Merchant |

FOREIGN PATENT DOCUMENTS

| | | |
|---|---|---|
| EP | 0 681 817 A1 | 11/1995 |
| EP | 0 705 075 B1 | 4/1996 |
| FR | 2700260 | 7/1994 |
| FR | 2740325 | 4/1997 |
| GB | 2277034 | 10/1994 |
| WO | WO 97/25006 A1 | 7/1997 |

OTHER PUBLICATIONS

Incavo et al., "The Tibial Axis and Patellar Position in Knee Kinematics", The Journal of Arthoplasty vol. 17 No. 2: Abstracts from the AAHKS Eleventh Annual Meeting, Feb. 2002, pp. 243-244.

Incavo et al., "The Tibial Axis and Patellar Position in Knee Kinematics", Knee Society Interim Meeting, Sep. 2002, Philadelphia.

* cited by examiner

KNEE JOINT PROSTHESIS WITH A FEMORAL COMPONENT WHICH LINKS THE TIBIOFEMORAL AXIS OF ROTATION WITH THE PATELLOFEMORAL AXIS OF ROTATION

This application claims the benefit of U.S. Provisional Patent Application No. 60/518,351, filed Nov. 7, 2003.

BACKGROUND

1. Field of Invention

This invention relates to prosthetic devices for total knee arthroplasty (TKA).

2. Discussion of Related Art

Total knee arthroplasty (TKA) is a surgical procedure for replacing a patient's injured or damaged knee joint with an artificial knee joint. TKA may be used to relieve pain caused from osteoarthritis and rheumatoid arthritis. TKA may also be performed to ameliorate discomfort resulting from deformed and unstable knees, cartilage destruction, and severe patellofemoral arthritis. As known to those of skill in the art, other indications, such as severe trauma, may also be treated with total knee arthroplasty.

Total knee replacement (TKR) has been performed in damaged and diseased knees for many years. In TKA, the posterior cruciate ligament (PCL) may either be retained or resected. If the PCL is retained, a cruciate retaining (CR) TKR prosthesis is used; if the PCL is resected, a cruciate substituting (CS) TKR prosthesis is used. The indications for using either a CR prosthesis or a CS prosthesis are known to those of skill in the art.

A knee joint prosthesis generally comprises three parts: a femoral component, a tibial component, and a patellar component. However, an individual's natural patella may continue to be used in some situations rather than replacing it with a prosthetic patellar component.

The femoral component is generally "U" shaped and implanted on the end of a patient's femur to replace the damaged surfaces of the femur while maintaining a substantial amount of the patient's natural femur. The tibial component comprises a tray, which replaces the upper surface of a patient's tibia, and a stem used to anchor the tibial tray in the patient's natural tibia. Generally, the tibial component has a metallic base with a plastic spacer on the tibial tray that provides a smooth surface to facilitate movement between the femoral component and the tibial component. The patella has a contour which tracks a portion of the femoral component during flexion and extension.

In TKA, the damaged surfaces of the knee joint are surgically removed and replaced with artificial surfaces. In particular, the ends of the femur and tibia are cut away, and prosthetic femoral and tibial components are placed over the cut ends of the respective leg bones. Due to the constant movement of the femur, tibia, and patella with respect to one another, the particular alignment of the femoral and tibial components may affect the long-term success of TKA. It has been suggested that various factors, such as geometry and alignment of the femoral component, may be associated with unbalanced collateral ligaments, lift off of the femoral component relative to the tibial component during gait, and premature loosening and subsequent failure of the implant. The geometry and alignment of the femoral component may also be associated with subluxation or inadequate movement of the patellar component relative to the femur.

SUMMARY

One embodiment of the present invention is directed to a femoral component for a knee joint prosthesis. The femoral component comprises a medial condyle portion, a lateral condyle portion, and a patellar groove constructed and arranged to guide a patella during knee flexion and extension. The patellar groove extends from an anterior portion of the femoral component to a posterior portion of the femoral component between the medial condyle portion and the lateral condyle portion. The patellar groove extends from the anterior portion to the posterior portion along a circular patellar arc of constant radius.

Another embodiment of the present invention is directed to a femoral component for a knee joint prosthesis. The femoral component comprises a medial condyle portion, a lateral condyle portion, and a patellar groove. The medial condyle portion includes a medial posterior aspect with a curved contact surface, and has a medial geometric center defined by the curved contact surface of the medial posterior aspect. The lateral condyle portion includes a lateral posterior aspect with a curved contact surface, and has a lateral geometric center defined by the curved contact surface of the lateral posterior aspect. The femoral component has a femoral geometric center axis which extends through the medial and lateral geometric centers and corresponds to the geometrical center axis of a knee joint. The patellar groove is constructed and arranged to guide a patella during knee flexion and extension. The patellar groove extends along a curved patellar path from an anterior portion of the femoral component to a posterior portion of the femoral component between the medial condyle portion and the lateral condyle portion. The curved patellar path has an origin that is positioned anterior and proximal to the femoral geometric center axis.

A further embodiment of the present invention is directed to femoral component for a knee joint prosthesis. The femoral component comprises a medial condyle portion, a lateral condyle portion, and a patellar groove. The medial condyle portion includes a medial posterior aspect with a curved contact surface, and has a medial geometric center defined by the curved contact surface of the medial posterior aspect. The lateral condyle portion includes a lateral posterior aspect with a curved contact surface, and has a lateral geometric center defined by the curved contact surface of the lateral posterior aspect. The femoral component has a femoral geometric center axis which extends through the medial and lateral geometric centers and corresponds to the geometrical center axis of a knee joint. The patellar groove is constructed and arranged to guide a patella during knee flexion and extension. The patellar groove extends along a curved patellar path in a first plane between the medial condyle portion and the lateral condyle portion. The curved patellar path is oriented so that the first plane is parallel to a second plane which is perpendicular to the femoral geometric center axis and intersects the center of a femoral head when the femoral component is attached to a femur. The first plane is to be spaced from the second plane by an offset distance of approximately 6.6 mm in a lateral direction to approximately 3.1 mm in a medial direction.

BRIEF DESCRIPTION OF DRAWINGS

Various embodiments of the invention will now be described, by way of example, with reference to the accompanying drawings, in which.

DETAILED DESCRIPTION

One aspect of the present invention is directed to a knee joint prosthesis that is configured to orient the coronal, transverse, and para-sagittal positions of the femur, tibia, and patella relative to the geometrical center axis of the knee after surgery. Various embodiments of the present invention include a femoral component that may be configured to provide one or more desirable kinematic relationships with a tibial component and/or patella in a manner which corresponds to the flexion and extension motion of a natural knee joint.

In one embodiment, the femoral component may be configured so that the patella follows a substantially circular pathway during knee flexion and extension.

In one embodiment, the femoral component may be configured so that the patella follows a curved pathway during flexion and extension, and the curved pathway has an origin located anterior and proximal to the geometrical center axis of the knee.

In one embodiment, the femoral component may be configured so that the patella follows a curved pathway that lies in a plane which is parallel to and offset from a plane that extends through the center of the femoral head of a femur and is perpendicular to the geometrical center axis of the knee.

In one embodiment, the femoral component may be configured so that at least a portion of the patella substantially follows a pathway in a plane perpendicular to the geometrical center axis throughout knee flexion.

In one embodiment, the prosthesis may be configured such that after implantation, the anatomic axis of the tibia remains perpendicular to the geometrical center axis of the knee throughout knee flexion and extension.

It is to be appreciated that the femoral component may incorporate any one or combination of features to provide the desirable kinematic relationships, and that not all embodiments are limited to each feature. The femoral component may be configured for either a cruciate retaining total knee replacement or a cruciate substituting total knee replacement. The femoral component may be configured for symmetrical or asymmetrical total knee replacement.

Figure 1:
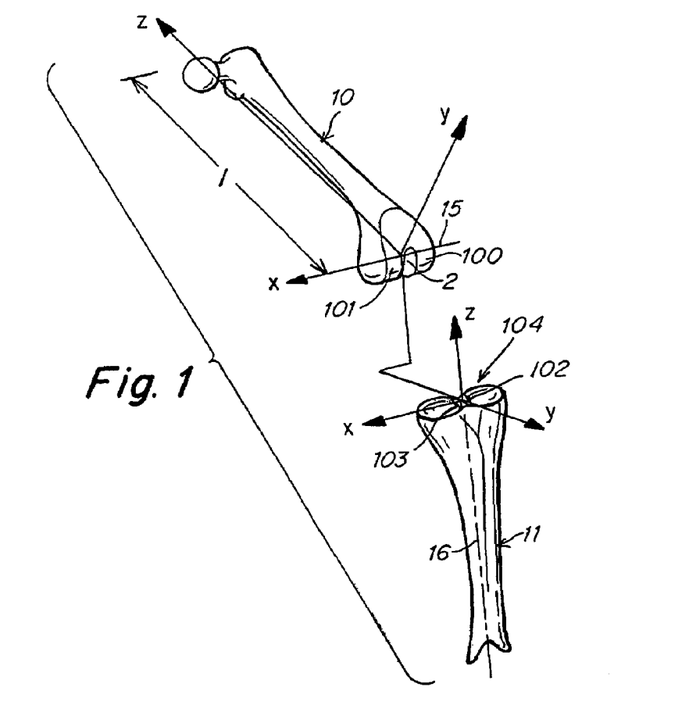
FIG. 1 is an exploded perspective view of a left knee joint with a femur and a tibia.

As illustrated in FIG. 1, a human leg comprises a femur 10 and a tibia 11. The femur 10 has a longitudinal aspect defining its length l. The distal (lower) portion of the femur 10 includes a lateral condyle 100 and a medial condyle 101. The tibia has a tibial axis 16 which passes through the center of the ankle joint and a point midway between the lateral eminence 102 and the medial eminence 103 of the tibial plateau 104.

Figure 2:
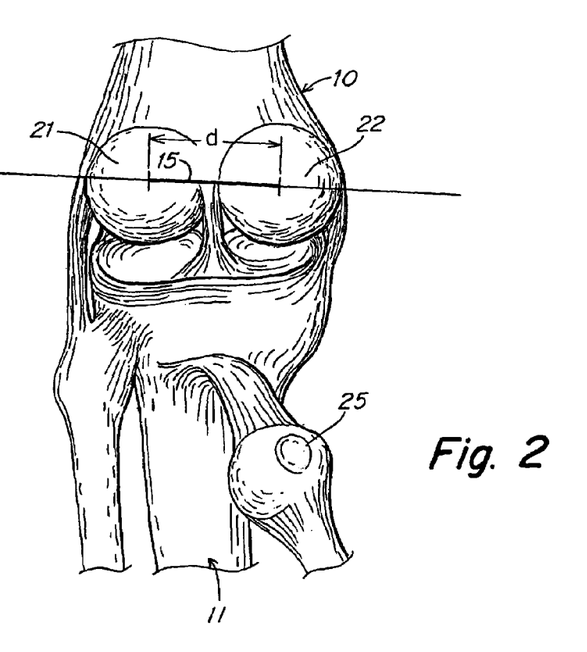
FIG. 2 is a front view of a right knee joint illustrating the geometrical center axis of the knee joint.

A knee joint includes a geometrical center axis 15 that extends between the geometrical centers of the posterior aspects of the lateral condyle 100 and the medial condyle 101. More particularly, the articulating or contact surfaces of the posterior aspects of the lateral condyle 100 and the medial condyle 101 each has a substantially spherical curvature which can be represented by a best fit sphere. As shown in FIG. 2, the posterior aspect of the lateral condyle may be represented by a lateral sphere 21 and the posterior aspect of the medial condyle may be represented by a medial sphere 22. The geometrical center axis 15 of the knee extends through the geometric centers of the lateral sphere 21 and the medial sphere 22.

The lateral sphere 21 corresponding to the posterior aspect of the lateral condyle 100 may have a different radius than the medial sphere 22 corresponding to the posterior aspect of the medial condyle 101. For example, the lateral sphere 21 may be smaller than the medial sphere 22. In an adult, the lateral sphere 21 has a radius of approximately 19 mm to approximately 27 mm with an average radius of approximately 24 mm. The medial sphere 22 has a radius of approximately 23 mm to approximately 31 mm with an average radius of approximately 27 mm.

Movement of the femur 10, tibia 11, and patella 25 during flexion and extension of a knee are described in an article entitled "Tibial Axis and Patellar Position Relative to the Femoral Epicondylar Axis during Squatting," Coughlin et al., J. Arthroplasty 18(8): 1048-1055 (2003), which is incorporated by reference as if recited in full herein.

Figure 3:
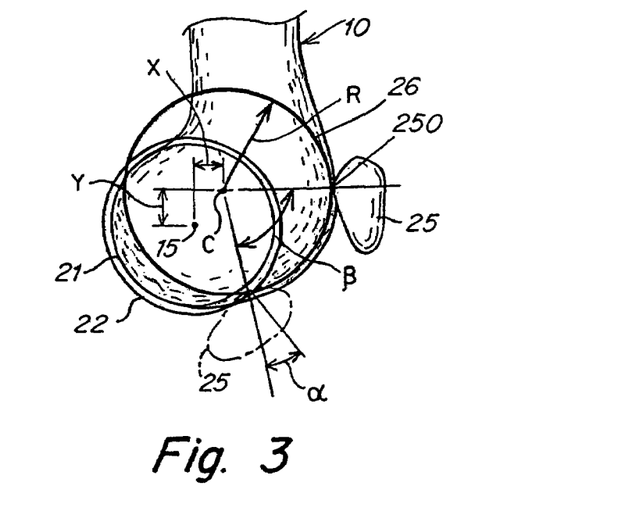
FIG. 3 is a side schematic view of a knee joint illustrating the patella and distal end of the femur in a direction along the geometrical center axis of the knee.

As illustrated in FIG. 3, the most prominent part 250 of the dorsal ridge of the patella 25 moves through an angle β as the knee flexes. When the knee flexes from full extension to 90 degrees of flexion, the patella moves through an angle β (patella relative to the femur) of approximately 110 degrees. The patella also rotates through an angle α (relative to its initial position) as it rotates through an angle β (patellar flexion).

The most prominent part of the dorsal ridge of the patella tracks a substantially circular path 26 in a plane that is oriented perpendicular to the geometrical center axis 15 of the knee as it moves through an angle β. The circular path 26 has an origin or center C with a radius R, as shown in FIG. 3. The origin C is located a distance X anterior and a distance Y proximal to the geometrical center axis 15 of the knee. In adults, the anterior distance X is approximately 7.0 mm to approximately 12.5 mm with an average anterior distance of approximately 9.6 mm. The proximal distance Y is approximately 8.3 mm to approximately 15.6 mm with an average proximal distance of approximately 11.6 mm.

Figure 4:
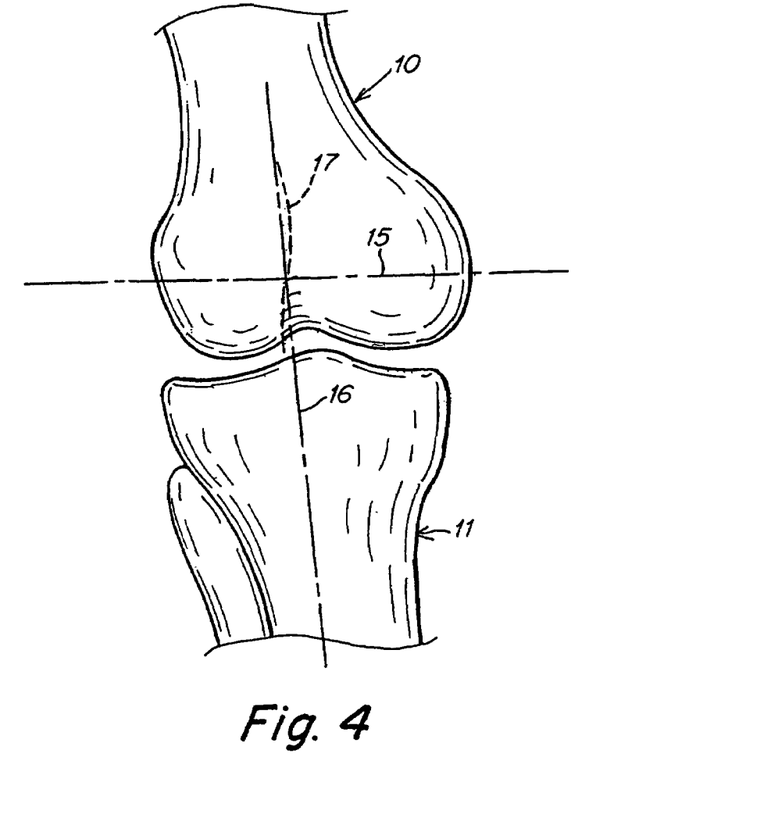
FIG. 4 is a front view of a knee joint illustrating the pathway of the most prominent part of the dorsal ridge of the patella during knee flexion and extension.

FIG. 4 illustrates the pathway 17 (dashed line) of the most prominent part of the dorsal ridge of the patella as the knee is flexed from full extension to 90 degrees of flexion. The pathway 17 of the patella 25 lies in a plane that is substantially perpendicular to the geometrical axis 15 of the knee through the entire range of knee flexion and extension.

Figure 5:
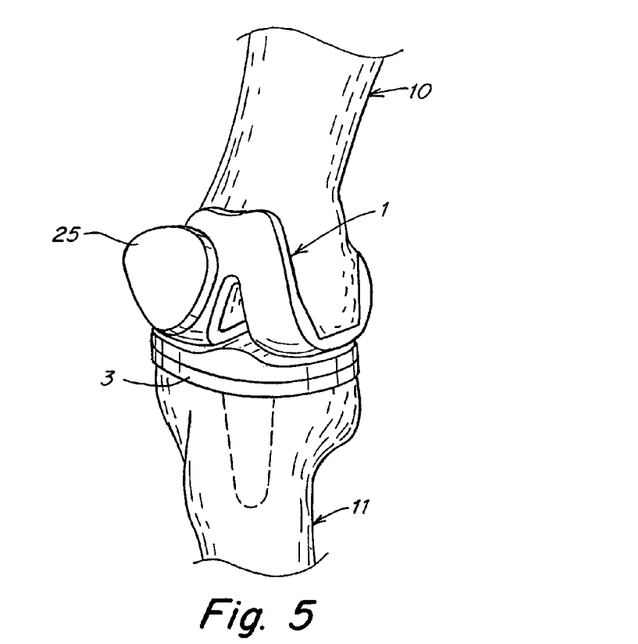
FIG. 5 is a front perspective schematic view of a knee joint prosthesis.

FIG. 5 illustrates one embodiment of a knee joint prosthesis. The knee joint prosthesis comprises a femoral component 1, a tibial component 3, and a patella 25. As used herein, "patella" refers to either a natural patella or a prosthetic patellar component.

Figure 6:
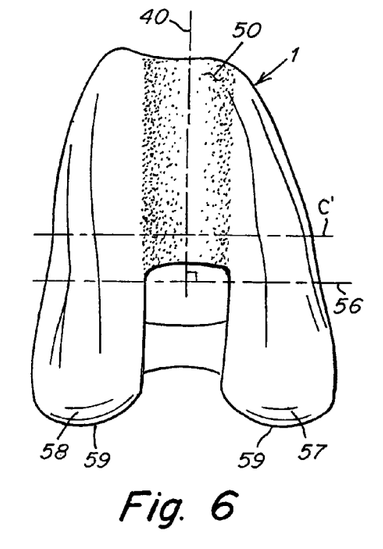
FIG. 6 is a front view of a femoral component according to one illustrative embodiment of the present invention.
Figure 7:
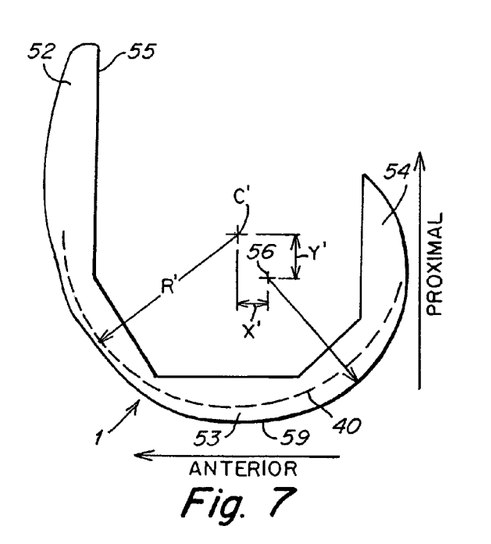
FIG. 7 is a side view of the femoral component of FIG. 6 in a direction along the femoral geometric center axis of the femoral component.

In one illustrative embodiment shown in FIGS. 6 and 7, the femoral component 1 is constructed and arranged so as to incorporate one or more of the above-described kinematic relationships of a natural knee joint.

The femoral component 1 has a substantially U-shaped configuration including an anterior portion 52, a distal portion 53, and a posterior portion 54. The femoral component 1 also includes a lateral condyle portion 57 and a medial condyle portion 58. Each of the posterior aspects of the medial and lateral condyle portions includes a curved contact surface 59 that is configured to bear on the tibial component during knee extension and flexion.

Each contact surface 59 may have a spherical curvature with a geometric center and a fixed radius that corresponds to the lateral and medial spheres 21, 22 of best fit for the lateral and medial condyles of a natural femur. In one embodiment, in a femoral component designed for use in an adult, the contact surface of the medial condyle portion 58 may have a radius of curvature of approximately 23 mm to approximately 31 mm. In another embodiment, the contact surface of the medial condyle portion may have a radius of curvature of approximately 24.6 mm to approximately 29.4 mm. In a further embodiment, the contact surface of the medial condyle portion may have a radius of curvature of approximately 27 mm. In one embodiment, the contact surface of the lateral condyle portion 57 may have a radius of curvature of approximately 19 mm to approximately 27 mm. In another embodiment, the contact surface of the lateral condyle portion may have a radius of curvature of approximately 22.2 mm to approximately 25.8 mm. In a further embodiment, the contact surface of the lateral condyle portion may have a radius of curvature of approximately 24 mm.

The distance between the geometric centers of the lateral and medial condyle portions may be varied to correspond to the size and shape of a natural femur. In one embodiment, the distance between the geometric centers of the lateral and medial condyle portions may be approximately 48 mm to approximately 58 mm. In another embodiment, the distance between the geometric centers of the lateral and medial condyle portions may be approximately 48.3 mm to approximately 55.7 mm. In a further embodiment, the distance between the geometric centers of the lateral and medial condyle portions may be approximately 52 mm.

Figure 8:
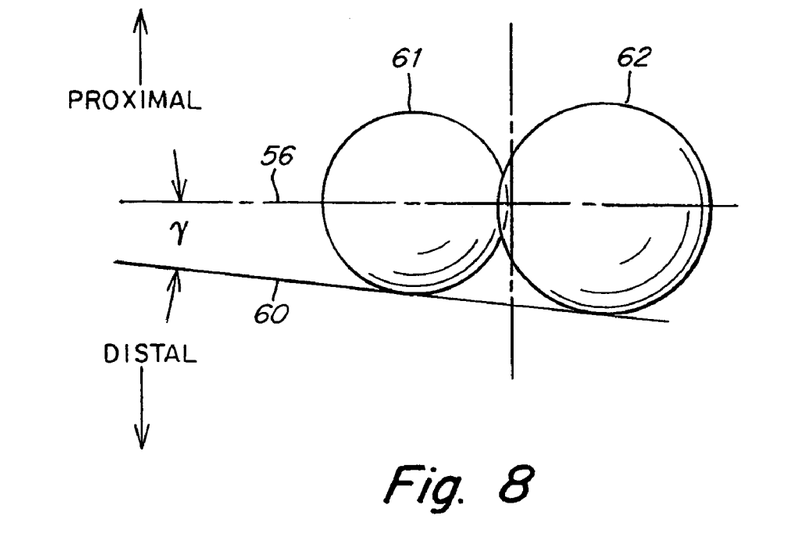
FIG. 8 is a schematic front view of the spheres of best fit for the lateral and medial condyle portions of the femoral component.

As shown in FIG. 8, the lateral and medial condyle portions of the femoral component may be represented by a lateral sphere 61 and a medial sphere 62. The lateral and medial spheres of the femoral component may define a femoral geometric center axis 56 and a tibiofemoral contact axis 60. The femoral geometric center axis extends through the geometric centers of the lateral and medial spheres. The tibiofemoral contact axis is tangent to both the lateral and medial spheres.

As shown in FIG. 6, the femoral component 1 includes a patellar path or groove 50 that extends from the anterior portion 52 to the posterior portion 54 between the medial and lateral condyle portions (FIG. 7). The patellar groove 50 is configured to provide a pathway for the patella 25 to track during flexion and extension of the knee when the femoral component 1 is attached to the femur of a patient. The patellar groove 50 may be configured to substantially replicate the kinematic relationships of a femur's trochlear groove 2 (see FIG. 1) when the femoral component 1 is properly attached to the distal portion of a femur. The patellar groove 50 may have any suitable cross sectional profile apparent to one of skill in the art. The groove may be configured to decrease contact stress between the femoral component 1 and the patella 25.

In one illustrative embodiment, the prosthetic patellar groove 50 may extend along a curved patellar path 40 that lies in a plane substantially perpendicular to the femoral geometric center axis 56. In this regard, when the femoral component 1 is properly positioned on a patient's femur 10, the patellar path will be oriented perpendicular to the natural geometrical center axis of the knee. Thus, the patellar groove will substantially track or guide the most prominent part of the dorsal ridge 250 of the patella 25 during flexion and extension in a manner that corresponds to a natural knee joint. It is to be appreciated that not all embodiments of the femoral component 1 are limited in this manner.

The curved patellar path 40 of the patellar groove may have a center or origin C' that is offset from the femoral geometric center axis. In one illustrative embodiment, the origin C' of the patellar path 40 may be located a distance X' anterior to the femoral geometric center axis and a distance Y' proximal to the femoral geometric center axis. In one embodiment, the center or origin C' of the patellar path may be positioned from approximately 5 mm to 15 mm anterior and approximately 6 mm to 18 mm proximal to the femoral geometric center axis. In another embodiment, the origin C' may be positioned approximately 7 mm to 13 mm anterior and approximately 8 mm to 16 mm proximal to the femoral center. In a further embodiment, the origin C' of the patellar path may be positioned approximately 9.6 mm anterior and approximately 11.6 mm proximal to the femoral geometric center axis. It is to be appreciated that any suitable offset between the origin C' of the patellar path and the femoral geometric center axis of the femoral component may be employed as would be apparent to one of skill in the art. Additionally, the anterior distance X' and the proximal distance Y' may be appropriately scaled for knee joint prostheses of different sizes as would be apparent to one of skill in the art.

The curved patellar path may extend along an arc of any suitable configuration for tracking the patella. In one illustrative embodiment, the patellar path 40 may extend along a circular arc. In this regard, the patellar path 40 extends along an arc of constant radius R' from the anterior portion 52 to the posterior portion 54 of the femoral component. In one embodiment, the radius R' of the patellar path 40 may be approximately 26.4 mm to approximately 34.7 mm. In another embodiment, the radius R' may be approximately 30.6 mm. It is to be appreciated that the patellar groove may be configured to extend along a circular path having any suitable radius R' as would be apparent to one of skill in the art.

Figure 9:
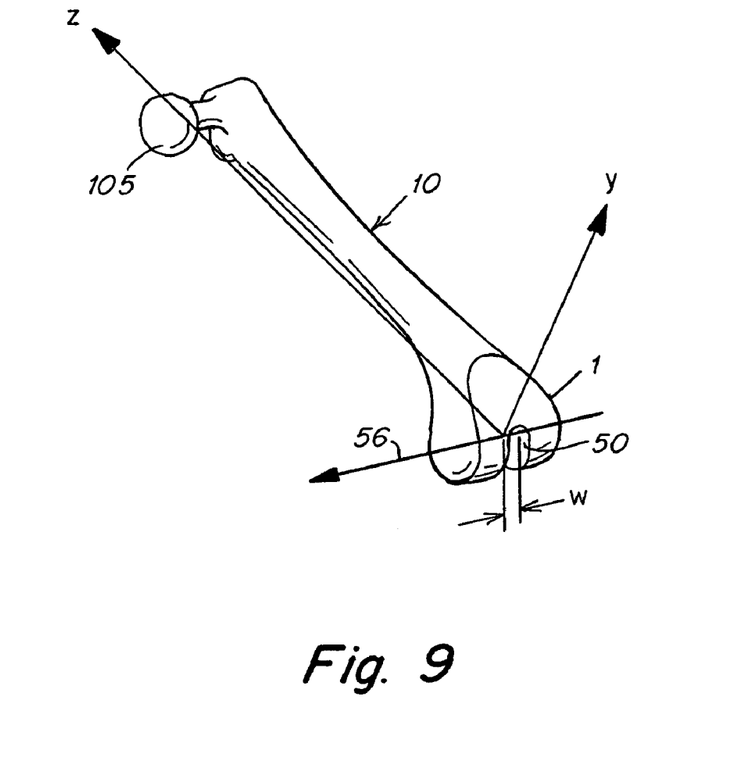
FIG. 9 is a schematic view of a femur with a femoral component.

The femoral component may be configured to position the patellar groove in a desirable medial-to-lateral position relative to the femur. As shown in FIG. 9, a y-z reference plane may be defined for the femur which extends through the center of the femoral head 105 and is oriented perpendicular to the geometrical center axis 15 of the knee. The femoral component 1 may be configured to position the patellar path 40 of the patellar groove 50 in a plane that is parallel to the reference plane and offset by a distance w from the reference plane when the femoral component is properly positioned on the distal portion of the femur. In one embodiment, the plane for the patellar path may be offset from the reference plane approximately 6.6 mm in a lateral direction to approximately 3.1 mm in a medial direction. In another embodiment, the plane for the patellar path may be offset from the reference plane approximately 1.2 mm in the lateral direction.

Depending on the size and spacing of the condyle portions, the femoral geometric center axis 56 and the tibiofemoral contact axis 60 may be oriented at an angle γ relative to each other. In one embodiment, the angle γ may be approximately 0° to approximately 6° in a coronal and/or transverse plane. In another embodiment, the angle γ may be approximately 2° to approximately 5.2° in a coronal and/or transverse plane. In a further embodiment, the angle γ may be approximately 3.6° in a coronal and/or transverse plane.

The femoral component may be configured with a femoral geometric center axis 56 which corresponds to the geometrical center axis 15 of the knee when the femoral component 1 is implanted on the distal end of the femur. A computer may be used to align the femoral geometric center axis with the geometrical center axis 15 of the knee. In one embodiment, a computer system may be utilized to digitize the three-dimensional spherical geometry of the posterior aspects of the condyles intraoperatively, and calculate the location of the geometrical center axis 15 of the knee. A physician may then use this information to prepare the femur for receipt of the femoral component so as to align the femoral geometric center axis 56 with the geometrical center axis 15 of the knee.

The femoral component 1 may be sized and configured to fit on the distal end of a patient's femur 10 after a damaged section of the patient's femur is removed. Techniques for fitting femoral components 1 to a patient's femur 10 during surgery are known. In one illustrative embodiment shown in FIG. 7, the interior surface 55 of the femoral component may be configured with a polygonal-like profile. However, the interior surface 55 of the femoral component may have any suitable configuration as would be apparent to one of skill in the art.

As would be apparent to one of skill in the art, the interior surface 55 of the femoral component may be designed and configured to compression fit the distal end of the femur. Additionally, or alternatively, the femoral component 1 may be configured to be mechanically secured to the patient's femur 10 using any suitable fastening arrangement. For example, cement such as polymethylmethacrylate (PMMA) may be used to secure the femoral component 1 onto the bone. If desired, the femoral component 1 may comprise a porous surface which permits bone ingrowth to the component. Other suitable methods for securing a prosthesis to bone are contemplated as would be apparent to one of skill in the art.

The femoral component may be configured for use in a cruciate retaining total knee replacement or a cruciate sustaining total knee replacement. In one embodiment illustrated in FIGS. 6-7, the femoral component is configured for use in a cruciate retaining total knee replacement. However, it is to be understood that not all embodiments are limited to a cruciate retaining femoral component.

The components of the knee joint prosthesis may be made of any suitable biocompatible material apparent to one of skill in the art. For example, metals, plastics, ceramics, and combinations of the above may be used to fabricate the various components. In one embodiment, the femoral component 1 may be formed of a metal, such as a stainless steel or a cobalt-chromium alloy. Alternatively or additionally, the femoral component 1 may comprise a ceramic material. The tibial component may additionally comprise a plastic material, such as polyethylene. Materials for the components of the prosthesis may be chosen in order to reduce friction and may alternatively or additionally be processed prior to implantation so that friction is reduced, such as through polishing. Coatings may additionally be applied to reduce surface friction.

The knee joint prosthesis according to the present invention may restore the normal strain distribution of the soft tissue structures that span the tibiofemoral and patellofemoral joints and guide joint motion. By aligning the femoral geometric center axis, the patellar axis and the tibial axis of the prosthesis with the axes of the patients' bones, the prosthesis may minimize pain to the patient as well as decrease the detrimental side effects associated with total knee arthroscopy. For example, the incidence of dislocation and failure may decrease due to improved tracking of the patellar component. The present invention may additionally benefit the post-surgical range of motion and collateral ligament balancing, thus potentially extending the life of the prosthesis.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A femoral component for a knee joint prosthesis, the femoral component comprising:
   a medial condyle portion including a medial posterior aspect with a curved contact surface, the medial condyle portion having a medial geometric center defined by the curved contact surface of the medial posterior aspect;
   a lateral condyle portion including a lateral posterior aspect with a curved contact surface, the lateral condyle portion having a lateral geometric center defined by the curved contact surface of the lateral posterior aspect, the femoral component having a femoral geometric center axis which extends through the medial and lateral geometric centers, the femoral geometric center axis corresponding to the geometrical center axis of a knee joint; and
   a patellar groove constructed and arranged to guide a patella during knee flexion and extension, the patellar groove extending along a curved patellar path from an anterior portion of the femoral component to a posterior portion of the femoral component between the medial condyle portion and the lateral condyle portion, the curved patellar path having a radius and being curved about an origin that is spaced from the curved patellar path by the radius, the origin being positioned anterior and proximal to the femoral geometric center axis.

2. The femoral component according to claim 1, wherein the origin of the curved patellar path is positioned from approximately 5 mm to approximately 15 mm anterior to the femoral geometric center axis.

3. The femoral component according to claim 2, wherein the origin of the curved patellar path is positioned from approximately 7 mm to approximately 13 mm anterior to the femoral geometric center axis.

4. The femoral component according to claim 3, wherein the origin of the curved patellar path is positioned approximately 9.6 mm anterior to the femoral geometric center axis.

5. The femoral component according to claim 2, wherein the origin of the curved patellar path is positioned from approximately 6 mm to approximately 18 mm proximal to the femoral geometric center axis.

6. The femoral component according to claim 1, wherein the origin of the curved patellar path is positioned from approximately 6 mm to approximately 18 mm proximal to the femoral geometric center axis.

7. The femoral component according to claim 6, wherein the origin of the curved patellar path is positioned from approximately 8 mm to approximately 16 mm proximal to the femoral geometric center axis.

8. The femoral component according to claim 7, wherein the origin of the curved patellar path is positioned approximately 11.6 mm proximal to the femoral geometric center axis.

9. The femoral component according to claim 1, wherein the curved patellar path lies in a plane that is perpendicular to the femoral geometric center axis.

10. The femoral component according to claim 1, wherein the curved patellar path has a constant radius of curvature of approximately 26 mm to approximately 35 mm.

11. The femoral component according to claim 1, wherein the contact surface of each of the medial and lateral posterior aspects has a spherical curvature.

12. The femoral component according to claim 1, wherein the contact surfaces of the medial and lateral condyle portions define a tibiofemoral contact axis, the femoral geometric center axis being oriented relative to the tibiofemoral contact axis at an angle of approximately 0° to approximately 6° in a coronal plane and/or a transverse plane.

13. The femoral component according to claim 12, wherein the angle is approximately 2° to approximately 5.2°.

14. The femoral component according to claim 13, wherein the angle is approximately 3.6°.

* * * * *